United States Patent [19]
Song et al.

[11] Patent Number: 5,874,230
[45] Date of Patent: Feb. 23, 1999

[54] ASSAYS USING TRAF2-ASSOCIATED PROTEIN KINASE POLYPEPTIDES

[75] Inventors: Yeong Song, S. San Francisco; Mike Rothe, San Mateo, both of Calif.

[73] Assignee: Tularik, Inc., South San Francisco, Calif.

[21] Appl. No.: 677,862

[22] Filed: Jul. 10, 1996

[51] Int. Cl.[6] .............................. C12N 9/12; C12Q 1/48
[52] U.S. Cl. .............................. 435/7.8; 435/7.1; 435/17; 435/194
[58] Field of Search ...................... 435/194, 325, 435/252.3, 320.1, 69.1, 7.1, 7.8, 17; 536/23.5, 24.3; 530/350

[56] References Cited

PUBLICATIONS

Frohman, M. in PCR Protocols: A Guide to Methods and Applications (1990) Innis, et al eds. pp. 28–38, Academic Press, Inc. San Diego, Calif.

Cheng et al. Isolation and mapping of human chromosome 21 cDNA. Genomics 23, 75, 1994.

Kentrup et al. (1996) J. Biol. Chem. 271, 3488–3495; "Dyrk, a Dual Specificity Protein Kinase with Unique Structural Features Whose Activity is Dependent on Tyrosine Residues between Subdomains VII and VIII"; see Figures 1 and 2 for sequence data.

*Primary Examiner*—David L. Fitzgerald
*Attorney, Agent, or Firm*—Richard Aron Osman

[57] ABSTRACT

A TRAF2 (Tumor Necrosis Factor receptor Associated Factor-2) kinase and DNA encoding it are described. The invention provides assays employing the TRAF2 kinase which are useful to identify candidate modulators of TRAF2-dependent signaling pathways.

17 Claims, 1 Drawing Sheet

ASSAYS USING TRAF2-ASSOCIATED PROTEIN KINASE POLYPEPTIDES

FIELD OF THE INVENTION

The field of this invention is a class of human proteins involved in gene transcription.

BACKGROUND

Nuclear factor κB (NF-κB) is a homo- or heterodimer of members of the Rel family of transcriptional activators that is involved in the inducible expression of a wide variety of important cellular genes including numerous cytokines, cytokine receptors, major histocompatibility antigens, serum amyloid A protein, etc. as well as many viral genes including genes of HIV, SV40, cytomegalovirus, etc. Several tumor necrosis factor receptor-associated factor (TRAF) proteins have been identified and shown to be involved in the signaling of various cellular responses including cytotoxicity, anti-viral activity, immuno-regulatory activities and the transcriptional regulation of a number of genes.

Accordingly, the ability to exogenously modulate the activity of NF-κB and/or TRAF proteins would yield therapeutic application for numerous clinical indications. In addition, components of such pathways would provide valuable target reagents for automated, cost-effective, high throughput drug screening assays and hence would have immediate application in domestic and international pharmaceutical and biotechnology drug development programs. The present invention provides novel TRAF-2 associated kinase proteins which regulate TRAF-2 function, their use, e.g. in drug screens, and nucleic acids encoding the same.

RELEVANT LITERATURE

Kentrup et al. (1996) J. Biol. Chem 271, 3488–3495, report the existence of Dyrk, a rat protein kinase with sequence similarity with the human kinase disclosed herein.

SUMMARY OF THE INVENTION

The invention provides methods and compositions relating to a novel human TRAF2-associated protein kinase and gene. The subject kinase proteins comprise a functional domain of SEQ ID NO:2 distinguishable (e.g. in terms of sequence or function, such as binding specificity) from rodent homologs of the kinase. For example, SEQ ID NO:2, residues 1–158, 159–479 and 480–763 provide human-specific C, kinase and N domains, respectively. The invention also provides isolated hybridization probes and primers capable of specifically hybridizing with or amplifying the disclosed human kinase protein gene (SEQ ID NO:1), nucleic acids encoding the subject proteins, methods of making the subject proteins and nucleic acids, and methods of using the subject compositions in diagnosis (e.g. genetic hybridization screens for gene mutations), and in the biopharmaceutical industry (e.g. reagents for screening chemical libraries for lead compounds for a pharmacological agent useful in the diagnosis or treatment of disease associated with immune regulation).

DETAILED DESCRIPTION OF THE INVENTION

Figure 1:
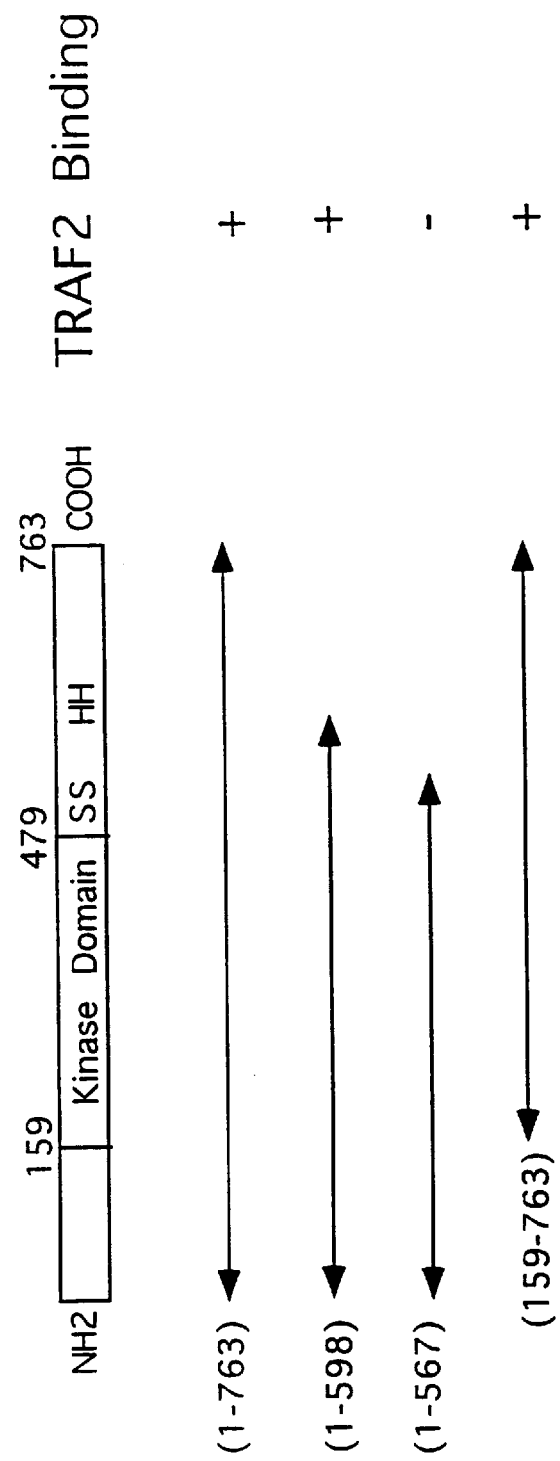
FIG. 1. Deletion mutant analysis of kinase proteins for TRAF2 binding.

The nucleotide sequence of a natural cDNA encoding a novel human TRAF2-associated protein kinase is shown as SEQ ID NO:1 and the full conceptual translate shown as SEQ ID NO:2. The kinase proteins of the invention include incomplete translates of SEQ ID NO:1 and deletion mutants of SEQ ID NO:2, which translates and deletions mutants have amino acid sequence and binding specificity or function different from rodent homologs of the protein. For example, the domain bound by residues 159 (Tyr) through 479 (Phe) of SEQ ID NO:2 defines an active kinase domain which may be used, independently or joined to other domains, in the subject methods; see FIG. 1. Also, an internal domain within residues 159–598 of SEQ ID NO:2 includes a TRAF-2 binding domain. This domain finds use in methods involving kinase-TRAF-2 complexes and may be used independently as a regulator of TRAF-2 activity, as a reagent in kinase complex formation assays, etc.

The binding or function specificity of the subject proteins necessarily distinguishes, qualitatively and/or quantitatively, rodent homologs (e.g. the rat Dyrk gene product). This specificity is especially important for screens for lead pharmaceuticals (below). Binding or function specificity may be determined by convenient in vitro, cell-based, or in vivo assays. Preferred proteins have kinase activity (e.g. autophosphorylate), specifically bind TRAF2 or modulate NF-κB activation. Such activity or function may be demonstrated in in vitro binding assays, in cell culture (e.g. cell transfections) or in animals (e.g. in vivo gene therapy, transgenics). Generally, binding specificity is shown by kinase activity, by binding equilibrium constants (usually at least about $10^7 M^{-1}$, preferably at least about $10^8 M^{-1}$, more preferably at least about $10^9 M^{-1}$) with natural binding targets such as hTRAF2 or nonnatural targets such as specific antibodies, by the ability of the subject protein to elicit a specific antibody in a rodent or rabbit (i.e. an antibody which distinguishes the subject proteins from rodent homologs), etc.

The claimed proteins are isolated or pure and are typically recombinantly produced. An "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. A wide variety of molecular and biochemical methods are available for generating, expressing and purifying the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provide binding agents specific to the subject kinase proteins including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g. NF-κB activation. Novel specific binding agents include specific antibodies and other natural intracellular binding agents identified with assays such as one-, two- and three-hybrid screens, non-natural intracellular binding agents identified in screens of chemical libraries such as described below, etc.

The invention also provides nucleic acids encoding the subject proteins, which nucleic acids may be part of expression vectors and may be incorporated into recombinant cells for expression and screening, transgenic animals for functional studies (e.g. the efficacy of candidate drugs for disease associated with signal transduction mediated by the subject kinase proteins), etc., and nucleic acid hybridization probes and replication/amplification primers having a cDNA specific sequence contained in SEQ ID NO:1 and sufficient to effect specific hybridization thereto (i.e. specifically hybridize with SEQ ID NO:1 in the presence of natural cDNAs encoding rodent homologs, eg. rat Dyrk cDNA (Kentrup et al., 1996, supra).

The subject nucleic acids are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a sequence joined to a nucleotide other than that which it is joined to on a natural chromosome. Nucleic acids comprising the nucleotide sequence of SEQ ID NO:1 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is immediately flanked by a sequence other than that which it is joined to on a natural chromosome. The subject nucleic acids find a wide variety of applications including use as translatable transcripts, hybridization probes, PCR primers, diagnostic nucleic acids, etc.; use in detecting the presence of the subject genes and gene transcripts and in detecting or amplifying nucleic acids encoding additional homologs and structural analogs. In diagnosis, the hybridization probes and/or primers find use in identifying wild-type and mutant alleles in clinical and laboratory samples. Mutant alleles are used to generate reagents e.g. allele-specific oligonucleotides (ASO), for high-throughput clinical diagnoses.

The invention provides efficient methods of identifying agents, compounds or lead compounds for agents active at the level of cellular function modulated by the disclosed protein kinases. Generally, these screening methods involve assaying for compounds which modulate interaction with a natural binding target. A wide variety of assays for binding agents are provided including labeled in vitro kinase assays, protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications may include infection, genetic disease, cell growth and regulatory disfunction, such as neoplasia, inflammation, hypersensitivity, etc.

In vitro binding assays employ a mixture of components including a subject protein kinase, which may be part of a fusion product with another peptide or polypeptide, e.g. a polypeptide that is capable of providing or enhancing protein-protein binding, stability under assay conditions, or a tag for detection or anchoring, etc. The assay mixtures comprise a natural intracellular specific-binding target, e.g. a substrate, such as TRAF2. A pseudosubstrate may be used or modified (e.g. A to S/T substitutions) to generate effective substrates for use in the subject kinase assays. While native binding targets may be used, it is frequently preferred to use portions (e.g. peptides, nucleic acid fragments) or analogs thereof so long as the portion or analog provides binding affinity and avidity to the subject protein kinase conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the kinase protein specifically binds the binding target, with a reference binding affinity. The mixture components can be added in any order that provides for the requisite bindings and incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the agent-biased binding between the kinase protein and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). For kinase assays, binding is detected by a change in the kinase-induced phosphorylation of the substrate.

Detection may be effected in any convenient way. For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

A difference in the binding affinity of the kinase protein to the target in the absence of the agent as compared with the binding affinity in the presence of the agent indicates that the agent modulates the binding of the kinase protein to the binding target. Analogously, in the cell-based transcription assay also described below, a difference in the transcriptional induction in the presence and absence of an agent indicates the agent modulates transcription induced by the subject kinase protein. A difference, as used herein, is statistically significant and preferably represents at least a 50%, more preferably at least a 90% difference.

The following experiments and examples are offered by way of illustration and not by way of limitation.

EXPERIMENTAL

A human kinase protein was initially identified in immunoprecipitates of TRAF2. Coprecipitating proteins were purified and subject to peptide sequencing. The resultant sequence data were used to design oligonucleotide probe and primers to isolate human cDNA clones. Identification was confirmed by overexpressing a full-length myc-tagged kinase-encoding cDNA in human 293 cells cotransfected with FLAG-tagged TRAF2 and immunoprecipitating the lysates with anti-FLAG then western blot analysis with anti-myc. A yeast two-hybrid system was also used to confirm TRAF2 binding and for deletion mutagenesis analysis of kinase. These experiments revealed that residues 1–763, residues 1–598 and residues 159–763 are each sufficient to mediate TRAF2 binding, while residues 1–567 is not. Human kinase peptides derived from the 567–598 are able to inhibit kinase-TRAF2 binding. Sequence analysis further define a kinase domain of residues 159–479. Recombinant kinase was prepared by over-expressing GST fusion proteins in *E. coli* and baculovirus expression systems.

EXAMPLES

1. Protocol for autophosphorylation assay.

A. Reagents

Neutralite Avidin: 20 μg/ml in PBS.

kinase: $10^{-8}$–$10^{-5}$M biotinylated kinase (SEQ ID NO:2) at 20 μg/ml in PBS.

Blocking buffer: 5% BSA, 0.5% Tween 20 in PBS; 1 hour at room temperature.

Assay Buffer: 100 mM KCl, 10 mM $MgCl_2$, 1 mM $MnCl_2$, 20 mM HEPES pH 7.4, 0.25 mM EDTA, 1% glycerol, 0.5% NP-40, 50 mM BME, 1 mg/ml BSA, cocktail of protease inhibitors.

$[^{32}P]\gamma$-ATP 10× stock: $2\times10^{-5}$M cold ATP with 100 μCi $[^{32}P]\gamma$-ATP. Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

B. Preparation of assay plates

Coat with 120 μl of stock N Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 40 μl biotinylated kinase (0.1–10 pmoles/40 ul in assay buffer)

Add 10 μl compound or extract.

Add 10 μl $[^{32}P]\gamma$-ATP 10× stock.

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls for all assays (located on each plate)
   a. Non-specific binding
   b. cold ATP at 80% inhibition.

2. Protocol for kinase protein—hTRAF2 complex formation assay

A. Reagents

Neutralite Avidin: 20 μg/ml in PBS.

Blocking buffer: 5% BSA, 0.5% Tween 20 in PBS; 1 hour at room temperature.

Assay Buffer: 100 mM KCl, 10 mM $MgCl_2$, 1 mM $MnCl_2$, 20 mM HEPES pH 7.6, 0.25 mM EDTA, 1% glycerol, 0.5% NP-40, 50 mM β-mercaptoethanol, 1 mg/ml BSA, cocktail of protease inhibitors.

$^{33}$P kinase protein 10× stock: $10^{-8}$–$10^{-6}$M "cold" kinase protein (SEQ ID NO:2, residues 159–598) supplemented with 200,000–250,000 cpm of labeled kinase protein (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

hTRAF2: $10^{-8}$–$10^{-5}$M biotinylated hTRAF2 in PBS.

B. Preparation of assay plates

Coat with 120 μl of stock N-Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 10 μl compound or extract.

Add 10 μl $^{33}$P-kinase protein (20,000–25,000 cpm/0.1–10 pmoles/well=$10^{-9}$–$10^{-7}$M final concentration).

Shake at 25° C. for 15 minutes.

Incubate additional 45 minutes at 25° C.

Add 40 μl biotinylated hTRAF2 (0.1–10 pmoles/40 ul in assay buffer)

Incubate 1 hour at room temperature.

Stop the reaction by washing 4 times with 200 μl PBS.

Add 150 μl scintillation cocktail.

Count in Topcount.

D. Controls for all assays (located on each plate)
   a. Non-specific binding
   b. Soluble (non-biotinylated hTRAF2) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of screening for a modulator of a TRAF2-dependent signaling pathway, comprising the steps of:
   (a) incubating a plurality of candidate modulators under suitable assay conditions with
      (i) a polypeptide comprising the amino acid sequence set forth in SEQ ID NO:2, or a fragment thereof which is capable of specifically interacting with TRAF2, and
      (ii) a species which specifically interacts with said polypeptide in the absence of the candidate modulators under said suitable assay conditions;
   (b) measuring the extent of the interaction between said polypeptide and said species in the presence of the candidate modulators;
   (c) selecting one or more candidate modulator(s) which perturb the interaction of said polypeptide and said species, relative to the extent to which they interact in the absence of the candidate modulators; and
   (d) assessing the affect of the one or more candidate modulators on the function of a TRAF2-dependent signaling pathway in an appropriate assay system.

2. A method according to claim 1, wherein said species is a TRAF2 polypeptide and said interaction comprises binding.

3. A method according to claim 1, wherein said polypeptide comprises at least the kinase domain of the protein represented by SEQ ID NO:2, said species is a kinase substrate, and said interaction comprises phosphorylation of the kinase substrate.

4. A method according to claim 3, wherein said polypeptide and said kinase substrate are the same and said interaction comprises autophosphorylation.

5. A method according to claim 1, wherein said polypeptide comprises residues 1–158, 159–479, or 480–763 as set forth in SEQ ID NO:2.

6. A method according to claim 2, wherein said polypeptide comprises residues 1–158, 159–479, or 480–763 as set forth in SEQ ID NO:2.

7. A method according to claim 3, wherein said polypeptide comprises residues 1–158, 159–479, or 480–763 as set forth in SEQ ID NO:2.

8. A method according to claim 4, wherein said polypeptide comprises residues 1–158, 159–479, or 480–763 as set forth in SEQ ID NO:2.

9. A method according to claim 1, wherein said polypeptide comprises SEQ ID NO:2.

10. A method according to claim 2, wherein said polypeptide comprises SEQ ID NO:2.

11. A method according to claim 3, wherein said polypeptide comprises SEQ ID NO:2.

12. A method according to claim 4, wherein said polypeptide comprises SEQ ID NO:2.

13. A method of screening for a modulator of a TRAF2-dependent signaling pathway, comprising the steps of:
(a) incubating a candidate modulator under suitable assay conditions with
  (i) a polypeptide comprising the amino acid sequence set forth in SEQ ID NO:2, or a fragment thereof which is capable of specifically binding to or phosphorylating TRAF2, and
  (ii) TRAF2;
(b) measuring the extent to which said polypeptide binds to or phosphorylates TRAF2 in the presence of the candidate modulator;
(c) determining whether the candidate modulator perturbs the binding or phosphorylation of TRAF2 by said polypeptide, relative to the extent of such binding or phosphorylation in the absence of the candidate modulator.

14. A method according to claim 13, wherein binding is measured.

15. A method according to claim 13, wherein said polypeptide comprises at least the kinase domain of the protein represented by SEQ ID NO:2 and wherein phosphorylation is measured.

16. A method according to claim 13, wherein said polypeptide comprises residues 1–158, 159–479, or 480–763 as set forth in SEQ ID NO:2.

17. A method according to claim 13, wherein said polypeptide comprises SEQ ID NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3218 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
ATGGAGCTCC   ACCGCGGTGG   CGGCCGCTCT   AGAACTAGTG   GATCCCCCAT   AGTTTTGCCG      60
CTGGACTCTT   CCCTCCCTTC   CCCCACCCCA   TCAGGATGAT   ATGAGACTTG   AAAGAAGACG     120
ATGCATACAG   GAGGAGAGAC   TTCAGCATGC   AAACCTTCAT   CTGTTCGGCT   TGCACCGTCA     180
TTTTCATTCC   ATGCTGCTGG   CCTTCAGATG   GCTGGACAGA   TGCCCCATTC   ACATCAGTAC     240
AGTGACCGTC   GCCAGCCAAA   CATAAGTGAC   CAACAGGTTT   CTGCCTTATC   ATATTCTGAC     300
CAGATTCAGC   AACCTCTAAC   TAACCAGGTG   ATGCCTGATA   TTGTCATGTT   ACAGAGGCGG     360
ATGCCCCAAA   CCTTCCGTGA   CCCAGCAACT   GCTCCCCTGA   GAAAACTTTC   TGTTGACTTG     420
ATCAAAACAT   ACAAGCATAT   TAATGAGGTT   TACTATGCAA   AAAAGAAGCG   AAGACACCAA     480
CAGGGCCAGG   GAGACGATTC   TAGTCATAAG   AAGGAACGGA   AGGTTTACAA   TGATGGTTAT     540
GATGATGATA   ACTATGATTA   TATTGTAAAA   AACGGAGAAA   AGTGGATGGA   TCGTTACGAA     600
ATTGACTCCT   TGATAGGCAA   AGGTTCCTTT   GGACAGGTTG   TAAAGGCATA   TGATCGTGTG     660
GAGCAAGAAT   GGGTTGCCAT   TAAAATAATA   AAGAACAAGA   AGGCTTTTCT   GAATCAAGCA     720
CAGATAGAAG   TGCGACTTCT   TGAGCTCATG   AACAAACATG   ACACTGAAAT   GAAATACTAC     780
ATAGTGCATT   TGAAACGCCA   CTTTATGTTT   CGAAACCATC   TCTGTTTAGT   TTTTGAAATG     840
CTGTCCTACA   ACCTCTATGA   CTTGCTGAGA   AACACCAATT   TCCGAGGGGT   CTCTTTGAAC     900
CTAACACGAA   AGTTTGCGCA   ACAGATGTGC   ACTGCACTGC   TTTTCCTTGC   GACTCCAGAA     960
CTTAGTATCA   TTCACTGTGA   TCTAAAACCT   GAAAATATCC   TTCTTTGTAA   CCCCAAACGC    1020
AGTGCAATCA   AGATAGTTGA   CTTTGGCAGT   TCTTGTCAGT   TGGGGCAGAG   GATATACCAG    1080
TATATTCAGA   GTCGCTTTTA   TCGGTCTCCA   GAGGTGCTAC   TGGGAATGCC   TTATGACCTT    1140
GCCATTGATA   TGTGGTCCCT   CGGGTGTATT   TTGGTTGAAA   TGCACACTGG   AGAACCTCTG    1200
TTCAGTGGTG   CCAATGAGGT   AGATCAGATG   AATAAAATAG   TGGAAGTTCT   GGGTATTCCA    1260
CCTGCTCATA   TTCTTGACCA   AGCACCAAAA   GCAAGAAAGT   TCTTTGAGAA   GTTGCCAGAT    1320
GGCACTTGGA   ACTTAAAGAA   GACCAAAGAT   GGAAAACGGG   AGTACAAACC   ACCAGGAACC    1380
CGTAAACTTC   ATAACATTCT   TGGAGTGGAA   ACAGGAGGAC   CTGGTGGGCG   ACGTGCTGGG    1440
GAGTCAGGTC   ATACGGTCGC   TGACTACTTG   AAGTTCAAAG   ACCTCATTTT   AAGGATGCTT    1500
GATTATGACC   CCAAAACTCG   AATTCAACCT   TATTATGCTC   TGCAGCACAG   TTTCTTCAAG    1560
AAAACAGCTG   ATGAAGGTAC   AAATACAAGT   AATAGTGTAT   CTACAAGCCC   CGCCATGGAG    1620
CAGTCTCAGT   CTTCGGGCAC   CACCTCCAGT   ACATCGTCAA   GCTCAGGTGG   CTCATCGGGG    1680
ACAAGCAACA   GTGGGAGAGC   CCGGTCGGAT   CCGACGCACC   AGCATCGGCA   CAGTGGTGGG    1740
CACTTCACAG   CTGCCGTGCA   GGCCATGGAC   TGCGAGACAC   ACAGTCCCCA   GGTGCGTCAG    1800
```

-continued

```
CAATTTCCTG CTCCTCTTGG TTGGTCAGGC ACTGAAGCTC CTACACAGGT CACTGTTGAA    1860
ACTCATCCTG TTCAAGAAAC AACCTTTCAT GTAGCCCCTC AACAGAATGC ATTGCATCAT    1920
CACCATGGTA ACAGTTCCCA TCACCATCAC CACCACCACC ACCATCACCA CCACCATGGA    1980
CAACAAGCCT TGGGTAACCG GACCAGGCCA AGGGTCTACA ATTCTCCAAC GAATAGCTCC    2040
TCTACCCAAG ATTCTATGGA GGTTGGCCAC AGTCACCACT CCATGACATC CCTGTCTTCC    2100
TCAACGACTT CTTCCTCGAC ATCTTCCTCC TCTACTGGTA ACCAAGGCAA TCAGGCCTAC    2160
CAGAATCGCC CAGTGGCTGC TAATACCTTG GACTTTGGAC AGAATGGAGC TATGGACGTT    2220
AATTTGACCG TCTACTCCAA TCCCCGCCAA GAGACTGGCA TAGCTGGACA TCCAACATAC    2280
CAATTTTCTG CTAATACAGG TCCTGCACAT TACATGACTG AAGGACATCT GACAATGAGG    2340
CAAGGGGCTG ATAGAGAAGA GTCCCCCATG ACAGGAGTTT GTGTGCAACA GAGTCCTGTA    2400
GCTAGCTCGT GACTACATTG AAACTTGAGT TTGTTTCTTG TGTGTTTTTA TAGAAGTGGT    2460
GTTTTTTTTC CAAAAACAAA GTGCAAAGCT GCTTGAATCA GGAGGAGATT AACACACTGA    2520
ACCGCTACAA GAGGGCAAAG CTGATTTTTT TTTTAACTTG AAAAGATTGC AAAGGGACAT    2580
TGAAGTGTTT AAAAGAGCCA TGTCCAAACC CATCTTCATG GATAGCTCAG AGGTATCCTC    2640
TTTTTGCTCC CCCATTTTAA CTTGCCACAT CCCAGTCACA GTGGGGTTTT TTTGTCTTTC    2700
TATTCAGCAA AAGTTAATAT TCAGATGTTG GTCTTGGTCA TTTGCCAACT AATTTTAAAG    2760
TAAAAGGCAC TGCACATAAT TTGCATAAAG GGCCCCATGA GGGTGTTTTT TTTTTTTCTT    2820
TTTGTCCCCC CCATCCCCCT TTTTTTTGT TTGTTCTGT TTTGTTTTGG GTGGGAGGGT    2880
GGGAAATTTG GGTTTTAAG TCCTCTAAAC ACACTTGGGC ACGGAAATGC AGTACTGTAA    2940
GGAANANGGA CCTCCAGCTT CCACAAACAC CATCTTCAGC TGTATGAAAG GGACGGTTGT    3000
GGTGAAGTTT GTCAGGCACA GTAAGCATGC TGAGTGGCGG GGATCAGAAC TCTCCTATCT    3060
GAACCTACTG AGGANCAAAG CAGCAATTAC ATGGATCCTG TGGCCNCCCC GTTGCAAAGC    3120
CCAGGAANAN AAGATGNACN TGACTGGTCT CCTAACCAAG TGCNCTGAAA ACCATCAACG    3180
GTCCGTCCTT GGCANTCCTG GGGAGTCTAA TTTGTGNC                           3218
```

( 2 ) INFORMATION FOR SEQ ID NO:2:

( i ) SEQUENCE CHARACTERISTICS:
    ( A ) LENGTH: 763 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:2:

```
Met His Thr Gly Gly Glu Thr Ser Ala Cys Lys Pro Ser Ser Val Arg
 1               5                  10                  15

Leu Ala Pro Ser Phe Ser Phe His Ala Ala Gly Leu Gln Met Ala Gly
            20                  25                  30

Gln Met Pro His Ser His Gln Tyr Ser Asp Arg Arg Gln Pro Asn Ile
            35                  40                  45

Ser Asp Gln Gln Val Ser Ala Leu Ser Tyr Ser Asp Gln Ile Gln Gln
        50                  55                  60

Pro Leu Thr Asn Gln Val Met Pro Asp Ile Val Met Leu Gln Arg Arg
65                  70                  75                  80

Met Pro Gln Thr Phe Arg Asp Pro Ala Thr Ala Pro Leu Arg Lys Leu
                85                  90                  95

Ser Val Asp Leu Ile Lys Thr Tyr Lys His Ile Asn Glu Val Tyr Tyr
```

-continued

|  |  |  |  |  | 100 |  |  |  |  | 105 |  |  |  |  | 110 |  |
|---|---|---|---|---|---|---|---|---|---|---|---|---|---|---|---|---|
| Ala | Lys | Lys 115 | Lys | Arg | Arg | His 120 | Gln | Gly | Gln | Gly | Asp 125 | Asp | Ser | Ser |
| His 130 | Lys | Lys | Glu | Arg | Lys 135 | Val | Tyr | Asn | Asp | Gly 140 | Tyr | Asp | Asp | Asn |
| Tyr 145 | Asp | Tyr | Ile | Val | Lys 150 | Asn | Gly | Glu | Lys | Trp 155 | Met | Asp | Arg | Tyr | Glu 160 |
| Ile | Asp | Ser | Leu | Ile 165 | Gly | Lys | Gly | Ser | Phe 170 | Gly | Gln | Val | Val | Lys 175 | Ala |
| Tyr | Asp | Arg | Val 180 | Glu | Gln | Glu | Trp | Val 185 | Ala | Ile | Lys | Ile | Ile 190 | Lys | Asn |
| Lys | Lys | Ala 195 | Phe | Leu | Asn | Gln | Ala 200 | Gln | Ile | Glu | Val | Arg 205 | Leu | Leu | Glu |
| Leu | Met | Asn 210 | Lys | His | Asp | Thr 215 | Glu | Met | Lys | Tyr | Tyr 220 | Ile | Val | His | Leu |
| Lys 225 | Arg | His | Phe | Met | Phe 230 | Arg | Asn | His | Leu | Cys 235 | Leu | Val | Phe | Glu | Met 240 |
| Leu | Ser | Tyr | Asn | Leu 245 | Tyr | Asp | Leu | Leu | Arg 250 | Asn | Thr | Asn | Phe | Arg 255 | Gly |
| Val | Ser | Leu | Asn 260 | Leu | Thr | Arg | Lys | Phe 265 | Ala | Gln | Gln | Met | Cys 270 | Thr | Ala |
| Leu | Leu | Phe 275 | Leu | Ala | Thr | Pro | Glu 280 | Leu | Ser | Ile | Ile | His 285 | Cys | Asp | Leu |
| Lys | Pro 290 | Glu | Asn | Ile | Leu | Leu 295 | Cys | Asn | Pro | Lys | Arg 300 | Ser | Ala | Ile | Lys |
| Ile 305 | Val | Asp | Phe | Gly | Ser 310 | Ser | Cys | Gln | Leu | Gly 315 | Gln | Arg | Ile | Tyr | Gln 320 |
| Tyr | Ile | Gln | Ser | Arg 325 | Phe | Tyr | Arg | Ser | Pro 330 | Glu | Val | Leu | Leu | Gly 335 | Met |
| Pro | Tyr | Asp | Leu 340 | Ala | Ile | Asp | Met | Trp 345 | Ser | Leu | Gly | Cys | Ile 350 | Leu | Val |
| Glu | Met | His 355 | Thr | Gly | Glu | Pro | Leu 360 | Phe | Ser | Gly | Ala | Asn 365 | Glu | Val | Asp |
| Gln | Met | Asn 370 | Lys | Ile | Val | Glu 375 | Val | Leu | Gly | Ile | Pro 380 | Pro | Ala | His | Ile |
| Leu 385 | Asp | Gln | Ala | Pro | Lys 390 | Ala | Arg | Lys | Phe | Phe 395 | Glu | Lys | Leu | Pro | Asp 400 |
| Gly | Thr | Trp | Asn | Leu 405 | Lys | Lys | Thr | Lys | Asp 410 | Gly | Lys | Arg | Glu | Tyr 415 | Lys |
| Pro | Pro | Gly | Thr 420 | Arg | Lys | Leu | His | Asn 425 | Ile | Leu | Gly | Val | Glu 430 | Thr | Gly |
| Gly | Pro | Gly 435 | Gly | Arg | Arg | Ala | Gly 440 | Glu | Ser | Gly | His | Thr 445 | Val | Ala | Asp |
| Tyr | Leu | Lys 450 | Phe | Lys | Asp | Leu | Ile 455 | Leu | Arg | Met | Leu 460 | Asp | Tyr | Asp | Pro |
| Lys 465 | Thr | Arg | Ile | Gln | Pro 470 | Tyr | Tyr | Ala | Leu | Gln 475 | His | Ser | Phe | Phe | Lys 480 |
| Lys | Thr | Ala | Asp | Glu 485 | Gly | Thr | Asn | Thr | Ser 490 | Asn | Ser | Val | Ser | Thr 495 | Ser |
| Pro | Ala | Met | Glu 500 | Gln | Ser | Gln | Ser | Ser 505 | Gly | Thr | Thr | Ser | Ser 510 | Thr | Ser |
| Ser | Ser | Ser 515 | Gly | Gly | Ser | Ser | Gly 520 | Thr | Ser | Asn | Ser | Gly 525 | Arg | Ala | Arg |

-continued

| Ser | Asp | Pro | Thr | His | Gln | His | Arg | His | Ser | Gly | Gly | His | Phe | Thr | Ala |
|---|---|---|---|---|---|---|---|---|---|---|---|---|---|---|---|
| | 530 | | | | 535 | | | | | | 540 | | | | |
| Ala | Val | Gln | Ala | Met | Asp | Cys | Glu | Thr | His | Ser | Pro | Gln | Val | Arg | Gln |
| 545 | | | | | 550 | | | | | 555 | | | | | 560 |
| Gln | Phe | Pro | Ala | Pro | Leu | Gly | Trp | Ser | Gly | Thr | Glu | Ala | Pro | Thr | Gln |
| | | | | 565 | | | | | 570 | | | | | 575 | |
| Val | Thr | Val | Glu | Thr | His | Pro | Val | Gln | Glu | Thr | Thr | Phe | His | Val | Ala |
| | | | 580 | | | | | 585 | | | | | 590 | | |
| Pro | Gln | Gln | Asn | Ala | Leu | His | His | His | His | Gly | Asn | Ser | Ser | His | His |
| | | 595 | | | | | 600 | | | | | 605 | | | |
| His | His | His | His | His | His | His | His | His | His | His | Gly | Gln | Gln | Ala | Leu |
| | 610 | | | | | 615 | | | | | 620 | | | | |
| Gly | Asn | Arg | Thr | Arg | Pro | Arg | Val | Tyr | Asn | Ser | Pro | Thr | Asn | Ser | Ser |
| 625 | | | | | 630 | | | | | 635 | | | | | 640 |
| Ser | Thr | Gln | Asp | Ser | Met | Glu | Val | Gly | His | Ser | His | His | Ser | Met | Thr |
| | | | | 645 | | | | | 650 | | | | | 655 | |
| Ser | Leu | Ser | Ser | Ser | Thr | Thr | Ser | Ser | Ser | Thr | Ser | Ser | Ser | Ser | Thr |
| | | | 660 | | | | | 665 | | | | | 670 | | |
| Gly | Asn | Gln | Gly | Asn | Gln | Ala | Tyr | Gln | Asn | Arg | Pro | Val | Ala | Ala | Asn |
| | | 675 | | | | | 680 | | | | | 685 | | | |
| Thr | Leu | Asp | Phe | Gly | Gln | Asn | Gly | Ala | Met | Asp | Val | Asn | Leu | Thr | Val |
| | 690 | | | | | 695 | | | | | 700 | | | | |
| Tyr | Ser | Asn | Pro | Arg | Gln | Glu | Thr | Gly | Ile | Ala | Gly | His | Pro | Thr | Tyr |
| 705 | | | | | 710 | | | | | 715 | | | | | 720 |
| Gln | Phe | Ser | Ala | Asn | Thr | Gly | Pro | Ala | His | Tyr | Met | Thr | Glu | Gly | His |
| | | | | 725 | | | | | 730 | | | | | 735 | |
| Leu | Thr | Met | Arg | Gln | Gly | Ala | Asp | Arg | Glu | Glu | Ser | Pro | Met | Thr | Gly |
| | | | 740 | | | | | 745 | | | | | 750 | | |
| Val | Cys | Val | Gln | Gln | Ser | Pro | Val | Ala | Ser | Ser | | | | | |
| | | 755 | | | | | 760 | | | | | | | | |